United States Patent [19]

Sakagami et al.

[11] Patent Number: 6,057,296
[45] Date of Patent: May 2, 2000

[54] PLANT GROWTH FACTOR

[75] Inventors: Youji Sakagami; Yoshikatsu Matsubayashi, both of Aichi, Japan

[73] Assignee: Kyowa Hakko Kogyo Co., Ltd., Japan

[21] Appl. No.: 09/240,607

[22] Filed: Feb. 1, 1999

Related U.S. Application Data

[63] Continuation-in-part of application No. PCT/JP97/02669, Jul. 31, 1997.

[30] Foreign Application Priority Data

Aug. 2, 1996 [JP] Japan .................................. 8-205116

[51] Int. Cl.$^7$ .............................. A61K 38/06; C07K 5/08; C07K 5/087
[52] U.S. Cl. .......................... 514/18; 530/331; 435/410; 435/431
[58] Field of Search .................................. 530/331, 345; 514/18; 435/431, 410

[56] References Cited

FOREIGN PATENT DOCUMENTS

| 0 220 379 | 5/1987 | European Pat. Off. . |
| 0 448 093 A2 | 9/1991 | European Pat. Off. . |
| WO 94/11018 | 5/1994 | WIPO . |

OTHER PUBLICATIONS

K. Barlos et al., "Application of 2–chlorotrityl resin in solid phase synthesis of (Leu$^{15}$)–gastrin I and unsulfated cholecystokinin octapeptide", *International Journal of Peptide and Protein Research* 38:555–561 (Dec. 1991).

R.L. Novak et al., "Tyrosyl Peptide Models for Acidic Protein–DNA Interactions", *Nature New Biology* 243:155–157 (1973).

Lou et al., Structure–Activity Relationship of a Novel Peptide Substrate for p60c–src Protein Tyrosine Kinase, Lett. Pept. Sci., 2(5):289; Chem. Abstr. No. 1996:86343 (1996).

Matsubayashi et al., Phytosulfokine, Sulfated Peptides that Induce the Proliferation of Single Mesophyll Cells of *Asparagus Officinalis* L., P.N.A.S. 93(15):7623 (1996).

Lam, K.S., et al., "The Chemical Synthesis of Large Random Peptide Libraries and Their Use for the Discovery of Ligands for Macromolecular Acceptors," *Bioorganic & Medicinal Chem . L.*, 3:419–424 (1993).

Karelin et al., Chem. Abstr. No. 1992:543989 (1992).

Teasdale, R. and Richards, D., "Study of a factor produced by suspension–cultured *Pinus radiata* cells which enhances cell growth at low inoculum densities," *Plant Cell, Tissue and Organ Culture*, 26:53–59 (1991).

Groeger et al., "Synthesis of pentapeptide analogs of dermorphin," *Zh. Obschch. Khim.*, 59(12) 2801–2 (1989) and translation; Chem. Abstr. No. 1990:424507 (1989).

Dyson, H.J., et al., "Folding of Immunogenic Peptide Fragments of Proteins in Water Solution," *J. Mol. Biol.*, 201:161–200 (1988); Chem. Abstr. No. 1988:469015 (1988).

Birnberg, P.R., et al., "Characterization of Conditioning Factors that Increase Colony Formation from <<Black Mexican Sweet Corn>> Protoplasts," *J. Plant Physiol.*, 132:316–321 (1988).

Bellincampi, D. and Morpurgo, G., "Conditioning Factor Affecting Growth in Plant Cells in Culture," *Plant Science*, 51:83–91 (1987).

Köhler, F. and Wenzel, G., "Regeneration of Isolated Barley Microspores in Conditioned Media and Trials to Characterize the Responsible Factor," *J. Plant Physiol.*, 121:181–191 (1985).

Echner et al., Synthesis and biological activity of new enkephalin derivatives, *Chem.–Ztg.* 107(11):340–42 (1983); Chem. Abstr. No. 1984:121586 (1983).

Novak et al., Chem. Abstr. No. 1975:150793 (1974).

Matsubayashi, et al., "Active Fragments and Analogs of the Plant Growth Factor, Phytosulfokine: Structure–Activity Relationships" Biochemical and Biophysical Research Commun., 1996, 225(1), 209–214.

*Primary Examiner*—Michael P. Woodward
*Assistant Examiner*—Anish Gupta
*Attorney, Agent, or Firm*—Finnegan, Henderson, Farabow, Garrett & Dunner, L.L.P.

[57] ABSTRACT

The present invention relates to a peptide of the formula:

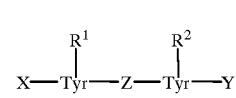

(I)

wherein both of $R^1$ and $R^2$ represent $SO_3H$, or either of $R^1$ or $R^2$ represents $SO_3H$ and the rest represents H; Z represents an α-amino acid residue; X represents H or an acyl; and Y represents OH, $C_{1-6}$ alkoxy or $NH_2$, and to a plant growth promoter comprising the peptide.

5 Claims, No Drawings

PLANT GROWTH FACTOR

This application is a Continuation-in-Part Application of PCT International Application No. PCT/JP97/02669, filed Jul. 31, 1997 and Japanese Application No. 205116/1996, filed Aug. 2, 1996, the contents of which are incorporated herein by reference.

TECHNICAL FIELD

The present invention relates to a plant growth promoter which is required for the plant growth and promotion.

BACKGROUND ART

The following plant-derived plant growth factors are known; barley-derived, fat-soluble fatty acid having a molecular weight of 600 or less [Journal of Plant Physiology, Vol. 121, pp. 181–191, 1985], pine-derived growth factor consisting of oligosaccharides having a molecular weight of 1000 or less [Plant Cell, Tissue and Organ Culture, Vol. 26, pp. 53–59, 1991], carrot-derived, heat-stable grow th factor having a molecular weight of about 700 [Plant Science, Vol. 51, pp. 83–91, 1987], and black Mexican maize-derived growth factor which has a molecular weight of 1350 or less, has oligosaccharide-like characteristics and is not adsorbed to either of anion-exchange resin or cation-exchange resin in a buffer at pH of 5 [Journal of Plant Physiology, Vol. 132, pp. 316–321, 1988].

It is difficult to isolate and purify such known plant-derived plant growth factors, and there is no known technique for mass-production of these factors. In order to use a plant growth factor as a plant growth promoter, there is a need to find out a mass-producible plant growth factor. In order to achieve industrial production, it is need to provide a lower molecular plant growth promoter.

DISCLOSURE OF THE INVENTION

The present invention relates to peptides of formula (I):

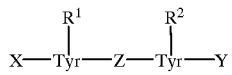

(I)

wherein both of $R^1$ and $R^2$ represent $SO_3H$, or either of $R^1$ or $R^2$ represents $SO_3H$ and the rest represents H; Z represents an α-amino acid residue; X represents H or an acyl; and Y represents OH, $C_{1-6}$ alkoxy or $NH_2$.

Compounds of formula (I) are hereinafter referred to as compound (I).

An α-amino acid in the α-amino acid residue includes aliphatic amino acids such as glycine, alanine, valine, leucine and isoleucine; hydroxyamino acids such as serine and threonine; sulfur-containing amino acids such as cysteine, cystine and methionine; acidic amino acids such as aspartic acid and glutamic acid; amido-amino acids such as asparagine and glutamine; basic amino acids such as lysine, arginine and ornithine; aromatic amino acids such as phenylalanine and tyrosine; and heterocyclic amino acids such as histidine, tryptophan, proline and hydroxyproline. Among these α-amino acids, preferred are aliphatic amino acids, especially preferred is valine and isoleucine. All of D-, L- or DL-amino acids may be used, preferably L-amino acids are used.

The acyl includes $C_{1-7}$ alkanoyl such as formyl, acetyl, propionyl, butyryl, isobutyryl, valeryl and pivaloyl; and aroyl such as benzoyl, toluoyl and naphthoyl.

Alkyl in the $C_{1-6}$ alkoxy is $C_{1-6}$ alkyl, for example, methyl, ethyl, propyl, isopropyl, butyl, tertiary butyl, pentyl and hexyl.

Compound (I) is a plant growth factor that can be obtained through ordinary peptide synthesis.

Compound (I) can be produced as follows: synthesizing a peptide skeleton according to peptide synthesis, which is referred to, for example, "Peptide Synthesis", in N. Izumiya et al. (published by Maruzen Publishing, in 1975), removing protecting groups for OH groups of tyrosine in a dehydrated, sulfonatedpeptide skeleton, and sulfonating the peptide skeleton using a sulfotransferase such as arylsulfatase or a sulfonating agent such as sulfonyl dimethylformamide to obtain compound (I).

The resulting compound (I) can be purified in any ordinary purification manner such as high-performance liquid chromatography.

Compound (I) can be used as a plant growth promoter as shown in the following embodiments.

(1) Liquid Preparations:

Compound (I) is dissolved in an aqueous solution containing a preservative and a pH adjusting agent at a concentration of 0.0001 to 1% to prepare a plant growth promoter. The preservative includes boric acid, bleaching powder, benzoic acid, salicylic acid, sorbic acid, dehydroacetic acid, propionic acid, isocyanuric acid, chlorous acid, hypochlorous acid, p-hydroxybenzoic acid and esters thereof, tribromosalicylanilide, 3,4,4'-trichlorocarbanilide, hexachlorophene, bithionol, chloramine-T, chloramine-B and halazone. Among these, preferred is sorbic acid. As a pH adjusting agent, any conventionally used pH adjusting agent such as citrates and phosphates can be used either singly or in combination.

The liquid preparation thus obtained is diluted with water from 100-fold to 10000-fold, preferably about 1000-fold. Plant seeds or seedlings such as cuttings are dipped in the resulting dilution, or the dilution is added to water cultures at a final concentration of the peptide of 0.001 to 10 ppm. In that manner, compound (I) can be used as a plant growth promoter.

(2) Paste Preparations:

A peptide of compound (I) is kneaded with a paste base at a concentration of 0.01 to 10 ppm to prepare a plant growth promoter. The paste base includes fats, fatty oils, lanolin, vaseline, paraffin, wax, resins, plastics, glycol, higher alcohols and glycerin. Among them, preferred are vaseline and lanolin.

The paste preparation thus obtained is applied to the grafted portions of grafts, or to the peduncles of fruits, or to the cut surfaces of cuttings. In that manner, compound (I) can be used as a plant growth promoter.

Embodiments of compound (I) are shown below.

[Compound (1)]

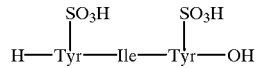

BEST MODES FOR CARRYING OUT THE INVENTION

The plant cell growth activity of the present plant growth factors is shown in the following test examples.

TEST EXAMPLE 1

(1) Preparation of Asparagus Single Cells:

The cladode of asparagus having a length of about 10 cm was used for both bioassay and preparing conditioned medium (CM). One cladode was used for bioassay and four cladodes were used for preparing 200 ml of CM. The collected cladodes were dipped in 70% ethanol for 30 seconds, then sterilized in a solution of 10-fold diluted antiformin containing Tween 20 (2 drops/100 ml) for 10 minutes, and thereafter washed three times with sterilized distilled water. Next, the cladodes were homogenized with sterilized distilled water using a glass homogenizer (22×167 mm; Iwaki Glass) on a clean bench. Then, the homogenate was filtered through a 37 µm stainless mesh (Iida Manufacturing), and the filtrate was centrifuged (100× g, 3 min; Kubota KS-5000) to precipitate the single cells. The precipitated single cells were again suspended in sterilized distilled water, and then centrifuged to remove the supernatant. This process was repeated three times, whereby impurities were completely removed from the cells.

(2) Preparation of Medium:

Just before use, the liquid medium having the composition shown in Table 1 was diluted with distilled water to have a concentration of 4-fold the intended concentration, adjusted to pH 5.8 with 1.0 N KOH, and then sterilized by filtering it through a sterilizing filter (ADVANTEC DISMIC-25cs, 0.20 µm).

The composition of the medium to be used here is shown in Table 1.

TABLE 1

Composition of Culture Medium

| Macro Elements (mg/liter) | | Micro Elements (mg/liter) | | Organic Components | |
|---|---|---|---|---|---|
| $KNO_3$ | 950 | $FeSO_4.7H_2O$ | 27.8 | Myo-inositol | 100 mg/liter |
| $NH_2NO_3$ | 825 | $EDTA.2Na.2H_2O$ | 37.3 | Thiamine | 0.1 mg/liter |
| $KH_2PO_4$ | 85 | $MnSO_4.H_2O$ | 16.9 | Glutamine | 1.0 g/liter |
| $CaCl_2.2H_2O$ | 220 | $ZnSO_4.7H_2O$ | 8.6 | Naphthalene- | 1.0 mg/liter |
| $MgSO_4.7H_2O$ | 185 | $H_3BO_3$ | 6.2 | acetic acid | |
| | | $CuSO_4.5H_2O$ | 0.025 | Benzyladenine | 0.3 mg/liter |
| | | $Na_2MoO_4.2H_2O$ | 0.25 | Sucrose | 10 g/liter |
| | | KI | 0.83 | Mannitol | 30 g/liter |
| | | $CoCl_2.6H_2O$ | 0.025 | | |

(3) Collection of CM:

The single cell suspension prepared above was conditioned to have a cell concentration of about $5.0 \times 10^5$ cells/ml, using a Bürker-Türk counting chamber (Nippon Rinsho Kikai Kogyo). To a 300-ml Erlenmeyer were put 50 ml of the suspension and 50 ml of the liquid medium having a 2-fold concentration (total: 100 ml), and sealed up with a silicone stopper. The cells were incubated in the dark at 28° C. with shaking at 120 rpm (TB-25R; Takasaki Kagaku Kikai). On the 10th day from the start of the incubation, the growth of the cells became the highest, CM was collected from the culture through suction filtration (ADVANTEC No. 2), then frozen and stored at −30° C.

(4) Preparation of Cultured Cells:

Single asparagus cells as obtained according to the method of (1) were implanted in the media, as prepared by the method of (2), and incubated with the present plant growth factor in the media. The influence of the plant growth factor on the proliferation of the incubated asparagus cells was determined by measuring the change in the colony formation frequency in each medium.

(i) Incubation of Cells:

Cells were incubated in a 24-well microtiter plate (IWAKI 3820-024). To each well of the microtiter were added 250 µl of a suspension of single asparagus cells as prepared at a cell density of 2-fold the intended final cell density, 125 µl of the liquid medium having a concentration of 4-fold of the intended final concentration, and 125 µl of sterilized distilled water or 125 µl of CM as obtained in (3) sterilized through filtration (ADVANTEC DISMIC-13cp, 0.20 µm) and diluted just before use, and fully stirred. Then, the plates were sealed with vinyl tape in order to prevent vaporization, in which the cells were incubated in the dark at 28° C. with shaking at 120 rpm (TAITEC BR-300L).

(ii) Observation of Cells:

Using an inverted microscope (100-magnification, OLYMPUS CK2), the number of the living cells (including the colony-forming cells), the number of the dead cells, and the number of the colony-forming cells, which were observed in the field of view, were counted for each well. On the basis of the data thus obtained for 3 wells or more, the colony formation frequency and the cell viability were calculated according to the following equations.

$$C\ (\%) = (a/b) \times 100$$

C: colony formation frequency
a: number of colony-forming cells
b: number of living cells $$L\ (\%) = [b/(b+d)] \times 100$$

L: cell viability
b: number of living cells
d: number of dead cells (iii) Effect of Compound (I) on Plant Cell Growth Activity (Colony Formation Frequency):

Compound (I) obtained in Example 1 and compound (a) obtained in Reference Example 1 were added to the single asparagus cells of $5 \times 10^4$ cells/ml and $2.5 \times 10^4$ cells/ml, at a final concentration of $10^{-5}$ to $10^{-9}$ M. Then the cells were incubated. The colony formation frequency of the asparagus cells at each concentration was measured and $ED_{50}$ was measured. The results are shown in Table 2.

TABLE 2

| Compound | Structure | $ED_{50}$ (nM) |
|---|---|---|
| Compound(1) | Tyr($SO_3H$)—Ile—Tyr($SO_3H$) | 20 |
| Compound(a) | Tyr($SO_3H$)—Ile | >1000 |

Table 2 indicates that compound (1) which is a tripeptide exhibits a remarkably high cell growth activity.

EXAMPLE 1

Compound (1) was prepared using peptide synthesis method in liquid phase as follows.

Fmoc-Tyr(t-Bu)-OBzl (wherein Fmoc represents 9-fluorenylmethoxycarbonyl, t-Bu represents tertiary butyl, and Bzl represents benzyl) was prepared from Fmoc-Tyr(t-Bu) (Peptide Association) in an ordinary manner [Dane et al., Journal of Organic Chemistry, Vol.47, pp.1962–1965, 1982]. Next, Fmoc-Ile (Peptide Association) and Fmoc-Tyr (t-Bu) were coupled with the Fmoc-Tyr(t-Bu)-OBzl successively by condensing agent, diethylphosphorocyanidate [NCP(O)(OC$_2$H$_5$)$_2$, hereinafter it is referred to as DEPC] in an ordinary manner [Nakao et al., Chemical Pharma Bulletin, Vol.37, pp.930–932, 1989]. A 95% trifluoroacetic acid solution was added to the resulting Fmoc-Tyr(t-Bu)-Ile-Tyr(t-Bu)-OBzl to remove t-Bu groups. The resulting Fmoc-Tyr(OH)-Ile-Tyr(OH)-OBzl was eluted through a silica gel chromatography using 9:1 chloroform-acetone as an eluent.

The resulting Fmoc-Tyr(OH)-Ile-Tyr(OH)-OBzl (35 mg, 0.1 mmol) was dissolved into 4:1 N,N-dimethylformamide (DMF)-pyridine, and 30 equivalents of sulfur trioxide-dimethylformamide (SO$_3$.HCON(CH$_3$)$_2$) was added thereto to react each other for 12 hours. After the reaction solution was concentrated, neutralized with a 10% ammonium hydroxide aqueous solution and then extracted with n-butanol. Among the remaining protecting groups, benzyl group was deprotected by catalytic hydrogenation (Niki et al., Journal of Chemical Society Perkin Transaction Vol.1, pp.1739–1744, 1990) and Fmoc group was deprotected by reaction with 50% piperidine-containing DMF for one hour. The resulting crude product was precipitated with 30 ml of cooled ether, dissolved with 20 ml of a 10% ammonium hydroxide aqueous solution. Then the resulting solution was applied to high-performance liquid chromatography using Develosil ODS-10 column (20×250 mm, Nomura Chemicals, Seto Japan). The compound was eluted with a 0.1% ammonium acetate aqueous solution containing 8% acetonitrile at a flow rate of 20 ml/min.

The structure of compound (1) was identified to be H-Tyr(SO$_3$H)-Ile-Tyr(SO$_3$H)—OH by FAB-MS analysis (pseudomolecular ion peak: m/z 638 [M−2H +Na]$^-$; molecular ion peak: m/z 616 [M−H]$^-$; and fragment ion m/z 536[M−H−SO$_3$]$^-$).

REFERENCE EXAMPLE 1

The procedure of Example 1 was repeated to prepare compound (a) having a structure of Tyr(SO$_3$H)-Ile, except that Fmoc-Tyr(t-Bu)-OBzl was reacted with only Fmoc-Ile using DEPC.

INDUSTRIAL APPLICABILITY

The present invention provides a mass-producible plant growth promoter having a high plant cell growth activity.

The present plant growth factor is effective to promote the growth of higher plants, especially monocotyledon including asparagus, rice and maize.

We claim:
1. A peptide of the formula:

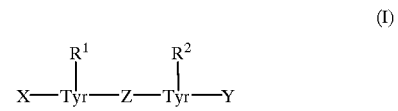

(I)

wherein R$^1$ and R$^2$ represent SO$_3$H or H, and wherein at least one of R$^1$ or R$^2$ is SO$_3$H; Z represents an α-amino acid residue; X represents H or an acyl; and Y represents OH, C$_{1-6}$ alkoxy or NH$_2$.

2. The peptide according to claim 1, wherein the α-amino acid residue represented by Z is an aliphatic amino acid residue.

3. The peptide according to claim 2, wherein the aliphatic amino acid residue is glycine residue, alanine residue, valine residue, leucine residue or isoleucine residue.

4. A plant growth promoter composition which comprises a peptide of the formula:

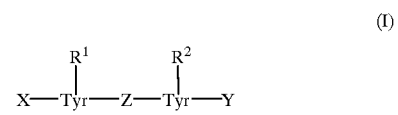

(I)

wherein R$^1$ and R$^2$ represent SO$_3$H or H, and wherein at least one of R$^1$ or R$^2$ is SO$_3$H; Z represents an α-amino acid residue; X represents H or an acyl; and Y represents OH, C$_{1-6}$ alkoxy or NH$_2$.

5. A method of promoting plant growth comprising administering to a plant a peptide of the formula:

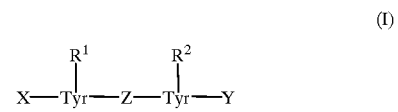

(I)

wherein R$^1$ and R$^2$ represent SO$_3$H or H, and wherein at least one of R$^1$ or R$^2$ is SO$_3$H; Z represents an α-amino acid residue; X represents H or an acyl; and Y represents OH, C$_{1-6}$ alkoxy or NH$_2$.

* * * * *